(12) United States Patent
Luzon et al.

(10) Patent No.: US 9,522,267 B2
(45) Date of Patent: Dec. 20, 2016

(54) TRANSDERMAL DELIVERY DEVICE

(75) Inventors: Josef Luzon, Bet Yehoshua (IL); Martin Gurovich, Tel Aviv (IL)

(73) Assignee: DERMA DREAM GROUP LTD, Tortola (VG)

( * ) Notice: Subject to any disclaimer, the term of this patent is extended or adjusted under 35 U.S.C. 154(b) by 245 days.

(21) Appl. No.: 13/609,552

(22) Filed: Sep. 11, 2012

(65) Prior Publication Data

US 2013/0204178 A1  Aug. 8, 2013

Related U.S. Application Data

(60) Provisional application No. 61/596,239, filed on Feb. 8, 2012.

(51) Int. Cl.
| | |
|---|---|
| *A61N 1/04* | (2006.01) |
| *A61N 1/05* | (2006.01) |
| *A61F 13/40* | (2006.01) |
| *A61N 1/32* | (2006.01) |
| *A61N 1/30* | (2006.01) |
| *A61M 35/00* | (2006.01) |
| *A61M 37/00* | (2006.01) |

(52) U.S. Cl.
CPC ............ *A61N 1/044* (2013.01); *A61N 1/0472* (2013.01); *A61N 1/303* (2013.01); *A61M 35/003* (2013.01); *A61M 35/006* (2013.01); *A61M 2037/0007* (2013.01); *A61M 2210/04* (2013.01); *A61N 1/0428* (2013.01); *A61N 1/0575* (2013.01); *A61N 1/30* (2013.01); *A61N 1/325* (2013.01)

(58) Field of Classification Search
CPC ........ A61N 1/30; A61N 1/044; A61N 1/0575; A61N 1/303; A61N 1/325; A61N 1/0428; A61M 35/00; A61M 35/003; A61M 35/006; A61M 2210/04; B05C 7/00
USPC .................................. 604/20, 290, 501, 21
See application file for complete search history.

(56) References Cited

U.S. PATENT DOCUMENTS

| | | | | |
|---|---|---|---|---|
| 5,421,816 A | * | 6/1995 | Lipkovker | 604/20 |
| 6,050,988 A | * | 4/2000 | Zuck | 604/890.1 |
| 6,835,184 B1 | * | 12/2004 | Sage et al. | 604/46 |
| 7,383,083 B2 | * | 6/2008 | Fischer et al. | 604/20 |
| 7,496,401 B2 | * | 2/2009 | Bernabei | 604/20 |

(Continued)

FOREIGN PATENT DOCUMENTS

| | | |
|---|---|---|
| CN | 101511425 A | 8/2009 |
| EP | 2198903 | 6/2010 |

(Continued)

OTHER PUBLICATIONS

International Search Report for Application No. PCT/IL2013/050103, mailed on May 28, 2013.

(Continued)

*Primary Examiner* — Imani Hayman
*Assistant Examiner* — Nilay Shah
(74) *Attorney, Agent, or Firm* — Pearl Cohen Zedek Latzer Baratz LLP

(57) ABSTRACT

A device includes a dispensing mechanism that is operable to dispense a substance from a canister that is connected to the device. The device includes at least one iontophoresis electrode that is chargeable to generate an electric field to enable transdermal delivery of an active ingredient of the substance when the substance is dispensed onto skin.

16 Claims, 6 Drawing Sheets

(56) References Cited

U.S. PATENT DOCUMENTS

| | | | |
|---|---|---|---|
| 2001/0037095 A1* | 11/2001 | Rucinski | A61M 3/02 604/319 |
| 2001/0055511 A1* | 12/2001 | Baumann et al. | 401/266 |
| 2002/0151937 A1* | 10/2002 | Ito | 607/20 |
| 2005/0267399 A1 | 12/2005 | Tedoldi | |
| 2009/0048556 A1* | 2/2009 | Durand | 604/20 |
| 2009/0204059 A1 | 8/2009 | Bernabei | |
| 2010/0022864 A1* | 1/2010 | Cordero et al. | 600/372 |
| 2010/0210993 A1 | 8/2010 | Flyash et al. | |
| 2011/0123252 A1* | 5/2011 | Thorpe | A45D 34/04 401/266 |
| 2011/0170934 A1 | 7/2011 | Ki | |

FOREIGN PATENT DOCUMENTS

| | | |
|---|---|---|
| EP | 2319577 | 5/2011 |
| EP | 2384789 | 11/2011 |
| GB | 2372705 | 9/2002 |
| JP | 2011-218041 | 11/2011 |
| WO | WO 00/10640 | 3/2000 |
| WO | WO 02/09807 | 2/2002 |

OTHER PUBLICATIONS

Office Action issued for Chinese Patent Application No. 201380018655.5, dated Nov. 4, 2015.
European Search Report of EP Application No. EP-13747205 mailed Feb. 5, 2016.

* cited by examiner

TRANSDERMAL DELIVERY DEVICE

CROSS REFERENCE TO RELATED APPLICATIONS

The present invention claims the priority benefit of U.S. provisional patent application No. 61/596,239 filed on Feb. 8, 2012, which is incorporated in its entirety herein by reference.

FIELD OF THE INVENTION

The present invention relates to a device for applying a substance to skin. More particularly, the present invention relates a device for transdermal delivery of a component of a substance.

BACKGROUND OF THE INVENTION

Various skin treatments include applying a substance or material to the skin. For example, the substance may be applied for the purpose of modifying or otherwise treating the skin so as to achieve a therapeutic or esthetic effect. The substance may variously be applied to the skin in the form of a cream, liquid, mist, patch, or powder.

The substance is typically applied topically to the outmost layer of the skin. The substance typically includes one or more active ingredients. The active ingredients are typically dissolved or suspended in a solvent liquid or gel.

However, in order for the applied substance to achieve its intended effect, one or more of the active ingredients may be required to penetrate into deeper layers of the skin, or into subcutaneous tissue or blood vessels. Such an active ingredient may include a medication or a bioactive material.

One technique used to cause an active ingredient of a topically applied substance to penetrate into the skin is iontophoresis. Topical application of a substance containing the active ingredient together with iontophoresis is sometimes utilized as a less invasive alternative to injection or similar techniques. With iontophoresis, molecules of the active ingredient that is to penetrate the skin are ionized. An electric field that is applied to the surface of the skin may then propel the ionized molecules through the skin and into subcutaneous tissue.

It is an object of embodiments of the present invention to provide a device for convenient delivery of an active ingredient of a topically substance through skin.

Other aims and advantages of embodiments of the present invention will become apparent after reading the present invention and reviewing the accompanying drawings.

SUMMARY OF THE INVENTION

There is thus provided, in accordance with some embodiments of the present invention, a device including: a dispensing mechanism that is operable to dispense a substance from a canister that is connected to the device; and at least one iontophoresis electrode that is chargeable to generate an electric field to enable transdermal delivery of an active ingredient of the substance when the substance is dispensed onto skin.

Furthermore, in accordance with some embodiments of the present invention, the dispensing mechanism includes an electric motor.

Furthermore, in accordance with some embodiments of the present invention, the dispensing mechanism includes a worm and nut.

Furthermore, in accordance with some embodiments of the present invention, the dispensing mechanism is configured to push a piston into the canister.

Furthermore, in accordance with some embodiments of the present invention, the device includes a plurality of channels through which the substance is dispensed upon operation of the dispensing mechanism.

Furthermore, in accordance with some embodiments of the present invention, the plurality of channels is interspersed with a plurality of the iontophoresis electrodes.

Furthermore, in accordance with some embodiments of the present invention, the plurality of channels is electrically isolated from the plurality of the iontophoresis electrodes.

Furthermore, in accordance with some embodiments of the present invention, the device includes an opening configured to enable a spout of the canister is configured to extend out of the device through the opening when the canister is installed in the device.

Furthermore, in accordance with some embodiments of the present invention, the dispensing mechanism is controllable to dispense a predetermined quantity of the substance.

Furthermore, in accordance with some embodiments of the present invention, a charge that is applied to the iontophoresis electrode is adjustable.

Furthermore, in accordance with some embodiments of the present invention, the device includes a return electrode that is configured such that when the iontophoresis electrode and the return electrode are placed in contact with separate regions of the skin, the skin completes an electrical circuit between iontophoresis electrode and the return electrode.

Furthermore, in accordance with some embodiments of the present invention, the return electrode is located on an outer surface of the device such that when the device is held in a hand, the hand contacts the return electrode.

Furthermore, in accordance with some embodiments of the present invention, the device includes a detector for detecting an identifying mark of the canister.

There is further provided, in accordance with some embodiments of the present invention, a method for transdermal delivery of an active ingredient of a substance, the method including: operating a dispensing mechanism of a transdermal delivery device so as to dispense the substance onto a region of skin, the substance including an active ingredient with ionized molecules; placing an iontophoresis electrode of the transdermal delivery device in contact with the region of the skin; and operating the transdermal delivery device to electrically charge the iontophoresis electrode with a charge whose sign is identical to a sign of a charge of the ionized molecules.

Furthermore, in accordance with some embodiments of the present invention, the method includes installing a canister that contains the substance in the transdermal delivery device.

Furthermore, in accordance with some embodiments of the present invention, operating the dispensing mechanism includes operating the dispensing mechanism to dispense a predetermined quantity of the substance.

Furthermore, in accordance with some embodiments of the present invention, the predetermined quantity is determined in accordance with a sensed characteristic of the skin.

Furthermore, in accordance with some embodiments of the present invention, the characteristic is selected from a group of characteristics consisting of temperature, moistness, impedance, and conductance.

Furthermore, in accordance with some embodiments of the present invention, the method includes placing a return electrode of the device in contact with a region of the skin that is separated from the region of the skin where the iontophoresis electrode is placed.

Furthermore, in accordance with some embodiments of the present invention, the method includes measuring an electrical current between the iontophoresis electrode and the return electrode.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

DETAILED DESCRIPTION OF EMBODIMENTS

Figure 1:
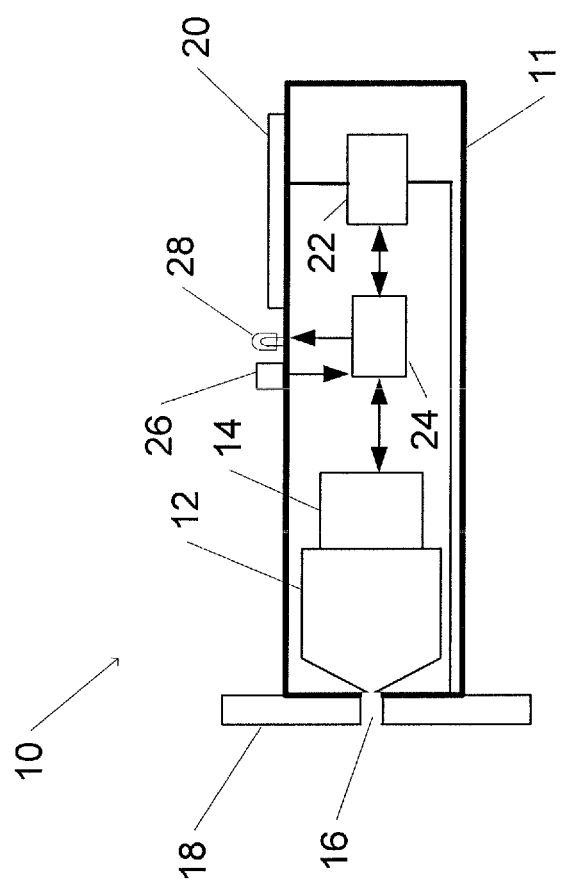
FIG. 1 is a schematic diagram of a transdermal delivery device in accordance with embodiments of the present invention.

In the following detailed description, numerous specific details are set forth in order to provide a thorough understanding of embodiments of the invention. However, it will be understood by those of ordinary skill in the art that the invention may be practiced without these specific details. In other instances, well-known methods, procedures, components, modules, units and/or circuits have not been described in detail so as not to obscure the invention.

In accordance with embodiments of the present invention, a transdermal delivery device includes a mechanism for topically applying a substance that includes a material, such as an active ingredient or other component, to skin. The transdermal delivery device also includes an iontophoresis system for causing the active ingredient of the topically applied substance to penetrate the skin. Any ingredient, component, material, or matter of a topically applied substance that is to be delivered through the skin by the transdermal delivery device is herein referred to as an active ingredient of the substance.

The applied substance typically includes a component or vehicle whose function includes facilitating topical application to the skin. For example, the vehicle may include a solvent in which the active ingredient is dissolved. The vehicle may include a liquid or viscous component in which the active ingredient is suspended in the form of a suspension or colloid. The active ingredient may include ionized molecules.

An iontophoresis electrode that is placed against the skin may be charged with a charge of the same sign as the charges of the ionized molecules of the active ingredient. Thus, the iontophoresis electrode may create an electric field that forces the ionized molecules toward and into the skin. Applying a charge of appropriate sign to the iontophoresis electrode may thus cause the ionized molecules of the active ingredient to penetrate the skin by iontophoresis (e.g. via spaces between adjacent skin cells). A return electrode (e.g. with charge opposite that of the iontophoresis electrode, or grounded) may be placed against the skin (e.g. at a distance from the iontophoresis electrode) so as to prevent buildup of charge on the skin (e.g. which could act to impede further iontophoresis). An electric current may thus flow between the iontophoresis electrode and the return electrode via the skin.

The transdermal delivery device may be configured for self-administration of the active ingredient by a user, or for administration by a non-professional user to the skin of another person (herein referred to as a patient), e.g. in a home environment. The material may be a drug or another material with a therapeutic or bioactive function.

The substance that is to be applied to the skin is contained within the device by a removable and replaceable container, canister, or cartridge (hereinafter referred to as a canister). The canister may be refillable (e.g. after removal from the transdermal delivery device). Access to the canister may be enabled by opening or removing a door, panel, or section of a housing of the transdermal delivery device. The transdermal delivery device includes structure for securely holding the canister in place within the transdermal delivery device. For example, one or more components of the structure may be openable or removable to enable replacement of the canister, and closable or replaceable so as to hold the replacement canister in place.

The transdermal delivery device may include a mechanism, such as an electromechanical mechanism, for dispensing the substance from the cartridge. For example, the canister may be provided with a plunger or piston that when pushed inward, forces the substance out of an opening of the canister. The substance dispensing mechanism may push on the piston so as to dispense the substance via the opening. As another example, one or more walls of the canister may be flexible. The substance dispensing mechanism may enable squeezing the flexible wall so as to force the substance out of an opening in the canister. Alternatively to, or in addition to, an electromechanical mechanism, a substance dispensing mechanism may include a manual mechanism (e.g. a surface on which a user may press so as to apply pressure to the canister), or a pneumatic or hydraulic system.

The transdermal delivery device may be sized and shaped to enable the transdermal delivery device to be conveniently and comfortably held, operated, and manipulated by a single hand. The transdermal delivery device may include a self-contained power source. The transdermal delivery device may be configured for convenient cleaning. For example, one or more panels or sections of a housing of the transdermal delivery device may be removable and washable.

FIG. 1 is a schematic diagram of a transdermal delivery device in accordance with an embodiment of the present invention.

When in use, transdermal delivery device 10 may be placed such that against skin such that iontophoresis electrode 18 and dispensing conduit 16 are placed against the skin. When in operation, a substance that is stored in canister 12 may be topically applied to the skin via dispensing conduit 16. The topically applied substance may include an active ingredient whose molecules are ionized. Iontophoresis electrode 18 may be charged with a charge of the same sign as that of the ionized molecules of the active ingredient. The charged iontophoresis electrode 18 may create an electrostatic field. The electrostatic field applies an electrostatic force on the ionized molecules of the active ingredient in the direction of the skin. Thus, the applied electrostatic force may cause the ionized molecules to penetrate the skin.

Transdermal delivery device 10 may include a feature for enabling determination of a quantity of the substance that is currently in canister 12. For example, in some embodiments of the present invention, part or all of canister 12 may be sufficiently transparent or translucent so as to enable ascertaining a level of a substance in the form of a liquid or gel within canister 12. In this case, housing 11 of transdermal delivery device 10 may be provided with an opening or a transparent window that enables viewing the level of the substance that is contained in canister 12.

In other embodiments, canister 12 or transdermal delivery device 10 may be provided with a sensor (e.g. mechanical, acoustic, optical, or electromagnetic) for sensing a quantity of the substance in canister 12. An indication of remaining quantity of the substance, or a warning that the remaining quantity of the substance in canister 12 is low, or that none of the substance remains, may be displayed or indicated, e.g. by indicator 28.

In accordance with yet another embodiment, a state of a dispensing mechanism 14 may be monitored in order to ascertain a quantity of the substance that remains in the canister. For example, a position or other state of a component of dispensing mechanism 14 may be provided with a sensor or encoder for determining its position. Such a component may include, for example, a motor, gear, worm, nut, shaft, cam, arm, lever, surface, or piston.

Canister 12 for holding a substance to be topically applied to the skin is removable. For example, when it is determined that the quantity of a substance in canister 12 is too low to enable proper delivery of the substance, canister 12 may be removed and another canister 12 installed in its place. Transdermal delivery device 10 may include structure that is configured to hold canister 12 in place within transdermal delivery device 10 or housing 11. The structure may be provided with a release mechanism for enabling easy removal of canister 12 from transdermal delivery device 10.

Canister 12 may be provided with a spout, or other form of opening or conduit, through which the substance is removed from canister 12 for dispensing.

In some embodiments of the present invention, a spout (or other opening) of canister 12 may couple to dispensing conduit 16. In this case, the coupling of the spout to dispensing conduit 16 may be provided with an appropriate seal (e.g. by an O-ring, gasket, sealing gel, or other sealing lining or structure) to prevent seepage of the substance into the interior of transdermal delivery device 10 or of housing 11.

In accordance with other embodiments, the spout may be elongated so as to extend outside of housing 11. For example, a dispensing conduit may include (or may consist solely of) an opening in housing 11 of transdermal delivery device 10. The spout may extend outward through the opening. Thus, when a substance is being dispensed from canister 12 (e.g. due to operation of dispensing mechanism 14), the substance may be applied from canister 12 directly onto skin that is near the opening. Direct dispensing of the substance from a spout of canister 12 (without any external conduit structure) may increase a number of uses of transdermal delivery device 10 prior to cleaning (e.g. may reduce or eliminate occurrences of the substance hardening within a conduit structure and thus impeding further dispensing of the substance).

Canister 12 may be configured such that a substance that is contained in canister 12 remains inside canister 12 unless pressure is applied to one or more surfaces of canister 12. For example, canister 12 may be designed such that a negative pressure (below ambient barometric pressure) is applied to the substance. The spout may be provided with a self-closing valve or flap that prevents the substance from seeping out of canister 12 through the spout.

Dispensing conduit 16 may include structure to facilitate effective application of the substance to the skin. For example, structure of dispensing conduit 16 may include a system of radiating or branching channels that are designed to evenly distribute the dispensed substance along and across iontophoresis electrode 18. The channel system may be designed to increase the spreading of a given quantity of the substance. Increasing the spreading may enable increasing the efficiency of utilization of the substance, thus the reducing the quantity of the substance that is dispensed. The channel system may be electrically isolated from iontophoresis electrode 18. The electrical isolation may prevent a charge that is applied to iontophoresis electrode 18 from inhibiting dispensing of the substance via the channel system or via dispensing conduit 16.

In order to dispense the substance from canister 12, pressure may be applied to one or more surfaces or components of canister 12. Dispensing mechanism 14 may be operated to apply pressure to the substance in canister 12. In some embodiments of the present invention, dispensing mechanism 14 may include a mechanical or electromechanical mechanism. An electromechanical mechanism may include an electric motor or actuator for moving one or more mechanical components. For example, an electric motor may cause a rotation of a shaft. A transmission may convert rotation of the shaft to a linear motion. A transmission may include, for example, a worm that is rotatable by the motor. Rotation of the worm may be converted to linear motion by a cooperating nut. The nut, or an element attached to or moved by the nut, may be pressed against the surface or component of canister 12. In other embodiments, an electromechanical mechanism may include a solenoid or linear actuator for causing linear motion of a shaft or axis. The shaft or axis, or an element attached to or moved by the shaft or axis, may be pressed against the surface or component of canister 12.

Pressing an element of dispensing mechanism 14 against an appropriate surface or component of canister 12 may increase the hydraulic pressure of the substance in canister 12. Increasing the hydraulic pressure of the substance in canister 12 may cause the substance to be dispensed from a spout of canister 12 via dispensing conduit 16.

Dispensing mechanism 14 may be configured to dispense a predetermined quantity of a substance from canister 12, or to dispense the substance from canister 12 at a predetermined rate. For example, operation of dispensing mechanism 14 may be controlled by controller 24. Controller 24 may be configured to control operation of dispensing mechanism 14 so as to precisely control a quantity of substance that is dispensed (e.g. at a single location on the skin) or rate of dispensing of the substance (e.g. if transdermal delivery device 10 is moved across the skin at an approximately constant rate or speed).

For example, a user may operate user control 26 of transdermal delivery device 10 (or another user interface to controller 24) so as to set a quantity or rate for dispensing the substance from canister 12. As another example, controller 24 or dispensing mechanism 14 may be configured to automatically dispense a quantity of the substance in accordance with predetermined conditions. Such conditions may include, for example, an elapsed time, a temperature of the skin or the substance, ambient humidity or moistness of the skin, or a quantity of the substance that remains in canister 12. Controller 24 or dispensing mechanism 14 may communicate with appropriate sensors for determine the conditions. The sensors may, for example, measure skin conditions such as temperature, moistness, elasticity, pH, or proximity to dispensing conduit 16. Dispensing mechanism 14 may be configured to dispense the substance only when contact with the skin is detected. For example, contact with the skin may be detected by a proximity or contact sensor (e.g. mechanical, acoustic, electromagnetic, or optical) or by detecting a closed circuit between iontophoresis electrode 18 and return electrode 20 via the skin.

Electrical system 22 may include a direct current voltage generation unit for applying an electrical charge to iontophoresis electrode 18. The sign of the charge that is applied to iontophoresis electrode 18 may be adjustable, e.g. so as to match a sign of ionized molecules of a particular active ingredient that is to be delivered by transdermal delivery device 10. Iontophoresis electrode 18 may be connected to an electrode of the voltage generation unit that is of the appropriate sign.

A voltage may be applied to return electrode 20 that is of a sign that is opposite the sign of the voltage that is applied to iontophoresis electrode 18. In another example, return electrode 20 may be grounded. When return electrode 20 is placed in contact with the skin, an electrical current may flow between iontophoresis electrode 18 and return electrode 20. Under some circumstances, in the absence of application of a return electrode 20 to the skin, a charge could build up in the skin that would weaken the electric field that is created by operation of iontophoresis electrode 18. Weakening of the electric field could inhibit the iontophoresis function of transdermal delivery device 10. Such circumstance may depend on such factors as the length of time that the electric field is applied and the conductivity of the skin in the vicinity of iontophoresis electrode 18.

Return electrode 20 may be placed in contact with the skin at a sufficient distance from iontophoresis electrode 18 so as to not interfere with iontophoresis. For example, when the user is operating transdermal delivery device 10 on the user's own skin, return electrode 20 may be placed in contact with a hand that is operating transdermal delivery device 10. If transdermal delivery device 10 is being operated by a user to deliver active ingredient to the skin of a patient who is not the user, return electrode 20 may be placed on a part of the skin where transdermal delivery device 10 is not being applied. In this case, the return electrode may be connected to electrical system 22 or to transdermal delivery device 10 by an appropriate cable.

Electrical system 22 may include circuitry for regulating a voltage that is applied to iontophoresis electrode 18 or to return electrode 20. Voltage regulation circuitry of electrical system 22 may be controlled so as to adjust the electrical field that is applied by iontophoresis electrode 18. Adjusting the electrical field may adjust transdermal penetration of the delivered active ingredient. For example, the voltage that is applied to iontophoresis electrode 18 may be adjusted by electrical system 22 or by controller 24. The electrical field may be adjusted in accordance with sensed or measured characteristics of the patient's skin. Such characteristics may include, for example, temperature, moistness, or skin impedance or conductance. The electrical field may be adjusted in accordance with a pre-defined sequence or protocol.

An electrical current between iontophoresis electrode 18 and return electrode 20 may be monitored. A measured current between iontophoresis electrode 18 and return electrode 20 may be indicative of a quantity of the substance that is dispensed on the skin. For example, a measured current that is smaller than a threshold value may be indicative of insufficient substance on the skin.

Iontophoresis electrode 18 may be shaped or sized so as to facilitate application to a variety of sites on the skin. Iontophoresis electrode 18 may be shaped or sized to facilitate application to skin on a particular limb or site. A surface of iontophoresis electrode 18 may be configured so as to facilitate iontophoresis or to facilitate a different or additional use of transdermal delivery device 10. For example, part or all of a surface of iontophoresis electrode 18 may be made abrasive. An abrasive surface of iontophoresis electrode 18 may be applied to the skin so as to exfoliate the skin. Utilization of an exfoliation function of transdermal delivery device 10 may be concurrent with, or separate from, utilization of transdermal delivery device for transdermal delivery of an active ingredient of a substance.

Controller 24 of transdermal delivery device 10 may be configured to control operation of one or more components of dispensing mechanism 14 or of electrical system 22. Controller 24 may include circuitry (e.g. including an integrated circuit) that is configured to operate a component of dispensing mechanism 14 or of electrical system 22 in accordance with user input. Circuitry of controller 24 may include a processor that is configured to operate in accordance with programmed instructions. A processor of controller 24 may communicate with a non-volatile data storage device that stores programmed instructions or stored parameters for the operation of the processor. A processor or other component of controller 24 may be configured to communicate with a processor or other device that is external to controller 24 or to transdermal delivery device 10. For example, communication with an external device may enable modification of instructions or parameters for operation of controller 24.

Controller 24 may be configured to control operation in accordance with user input via a user control 26. User control 26 may include one or more physical controls (e.g. a pushbutton, dial, lever, key, or touch sensitive pad) or may include a graphic user interface together with screen navigation or pointing devices.

Controller 24 may be configured to operate an indicator 28. Indicator 28 may include one or more devices for generating a visible (e.g. light, display screen, or gauge) or audible (e.g. speaker, buzzer, or bell) signal. For example, controller 28 may operate indicator 28 so as to indicate a current state or operation of transdermal delivery device 10, to issue a warning, or to provide feedback to a user upon operation of a user control 26.

Controller 24 or electrical system 22 may include a power source. The power source may include an internal battery (e.g. rechargeable or replaceable), or may include a connection (e.g. via a power cable) to an external power source (e.g. an electrical power grid, power supply, transformer, or converter).

In accordance with an embodiment of the present invention, controller 24, electrical system 22, or dispensing mechanism 14 may include a timing mechanism. For example, a timer may be started or initialized when operation of dispensing mechanism 14 for dispensing a substance, or operation of electrical system 22 to apply an electric charge to iontophoresis electrode 18 is started. An indicator 28 may be operated to indicate an elapsed time, or to indicate that a predetermined time has elapsed. A predetermined time may be selected in accordance with an applied substance, an active ingredient of the applied substance, or in accordance with one or more characteristics of the skin or of the patient.

In accordance with an embodiment of the present invention, controller 24 or transdermal delivery device 10 may be configured to automatically identify a canister 12. For example, a canister 12 may be marked so as to identify the contents of the canister 12. (In such a case, canister 12 is not refillable, or is refillable only in an authorized manner, or by a person or organization that is authorized to refill canister 12 only with a substance that is identical to the original contents. For example, a fixture or machine for refilling canister 12 may be constrained to refill canister 12 with a substance identical to the original contents. As another example, the fixture may remark canister 12 when canister 12 is refilled.)

For example, marking may include optical (e.g. stored in a barcode, color coding, gray scale coding, polarization, or other manner that may be queried optically), electronic (e.g. identification data stored in an electronic component of canister 12), or electromagnetic (e.g. with a radiofrequency identification tag) marking or coding. An appropriate optical (e.g. optical barcode reader, photo-sensitive detector, color or reflectance meter, polarized detector, e.g. in conjunction with a appropriate light source) or electromagnetic (e.g. radiofrequency identification reader) detector, or an appropriate data or communications interface (e.g. data or communications port or connector, or communications port or connector) in transdermal delivery device 10 may be utilized to read the marking or identification data. Information included in the marking may identify a substance or active ingredient that is contained by canister 12, a quantity of substance that is contained in canister 12, or instructions or parameters for delivery of the substance or the active ingredient.

Controller 24 may be configured to operate dispensing mechanism 14 or electrical system 22 in accordance with information that is encoded in a marking of canister 12. For example, information that is encoded in the marking may be utilized in determining or defining a duration of dispensing the substance, a duration of performing iontophoresis, a sign of a generated electrical field (or charge), a magnitude of a generated electrical field (or charge), a generated magnetic field, or a quantity of substance to be dispensed (or a dispensing rate). Controller 24 may operate an indicator 28 in accordance with information that is encoded in the marking. Data may be communicated to a data storage device of canister 12, e.g. to update a quantity of a substance that remains in canister 12. Inability to read or interpret information that is encoded in the marking may be indicative that the canister is not loaded into transdermal delivery device 10, or that it is loaded improperly.

Figure 2A:
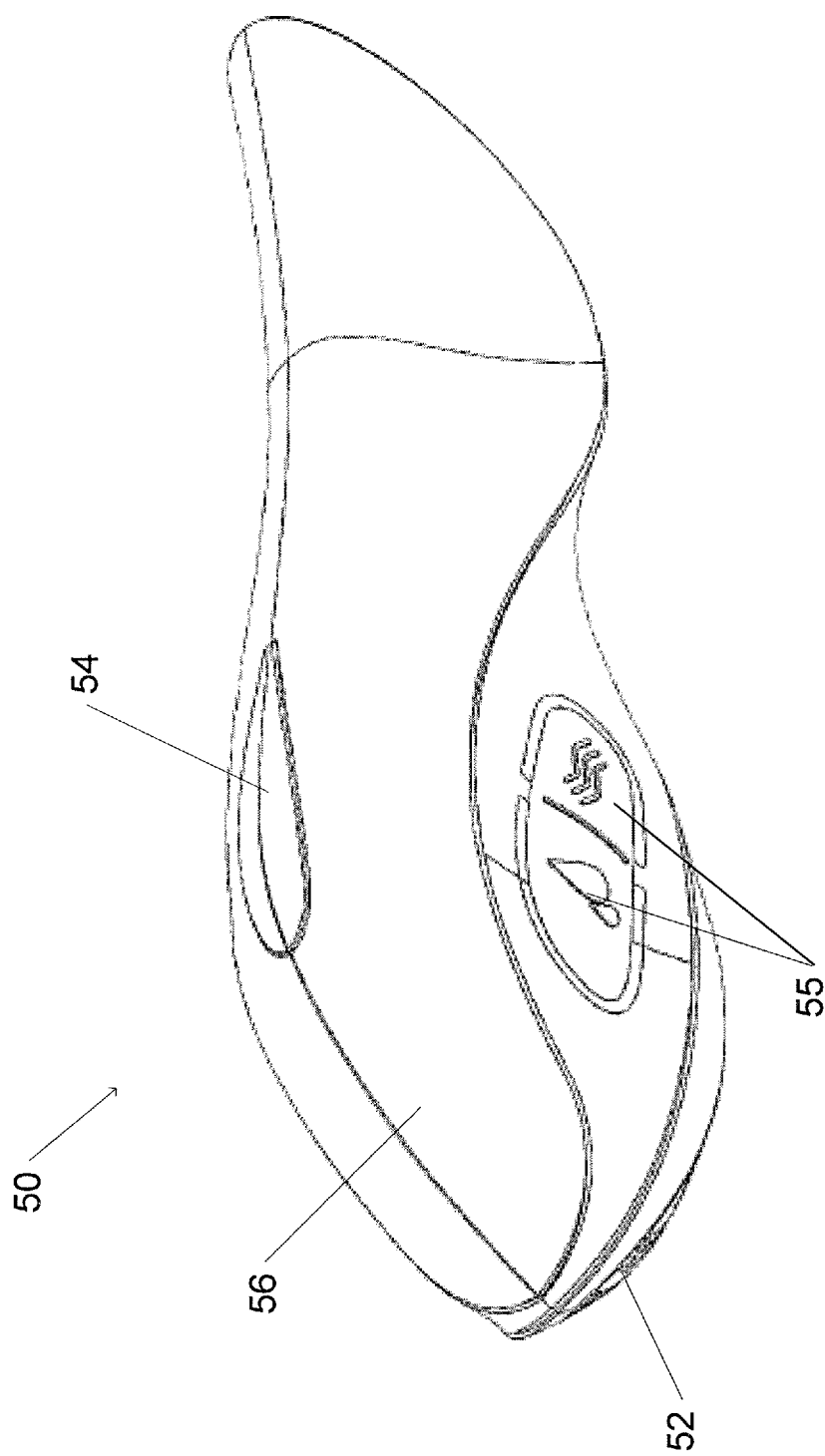
FIG. 2A shows a transdermal delivery device in accordance with an embodiment of the present invention.
Figure 2B:
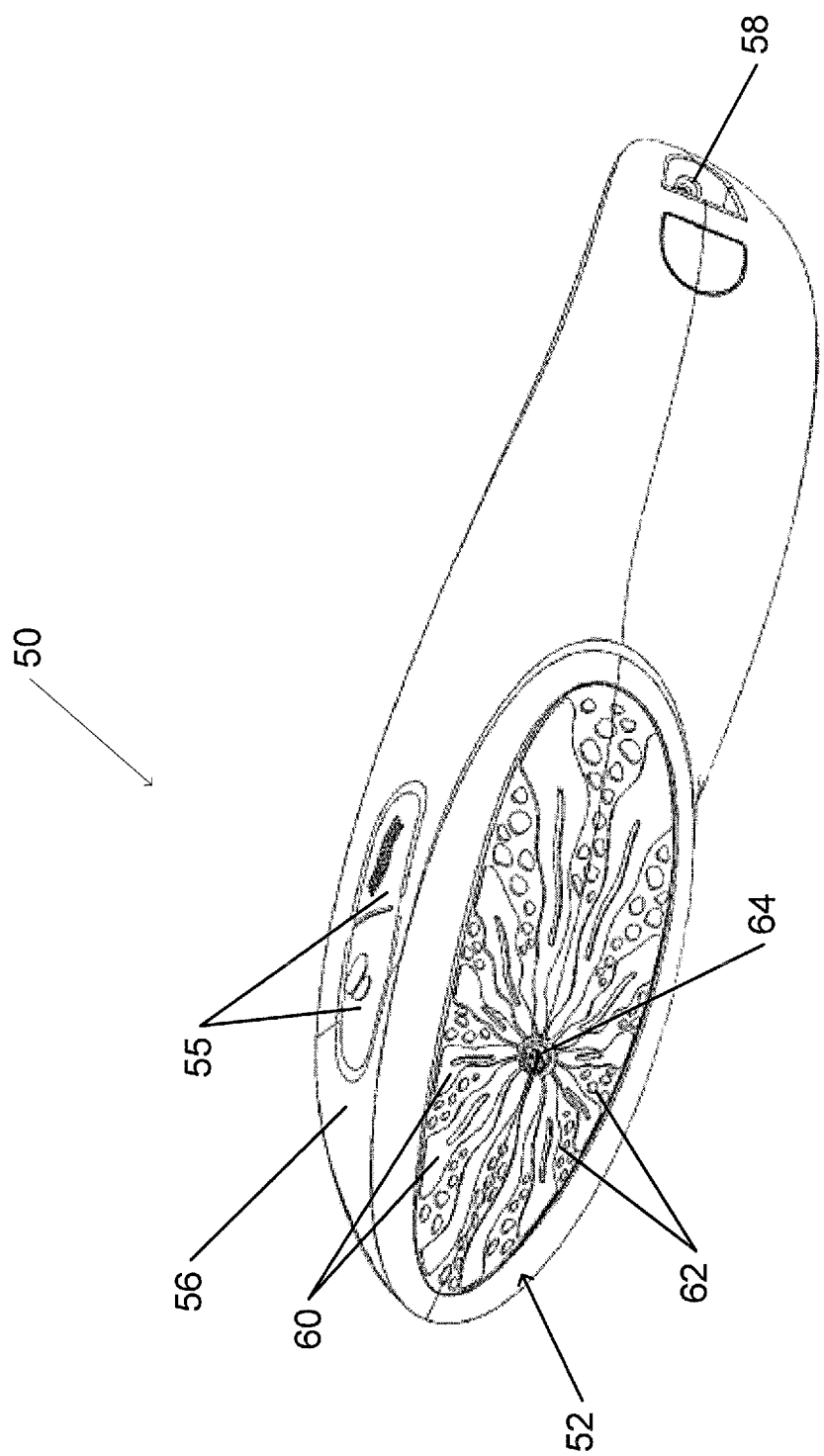
FIG. 2B shows another view of the transdermal delivery device shown in FIG. 2A in which the iontophoresis electrode is visible.
Figure 2C:
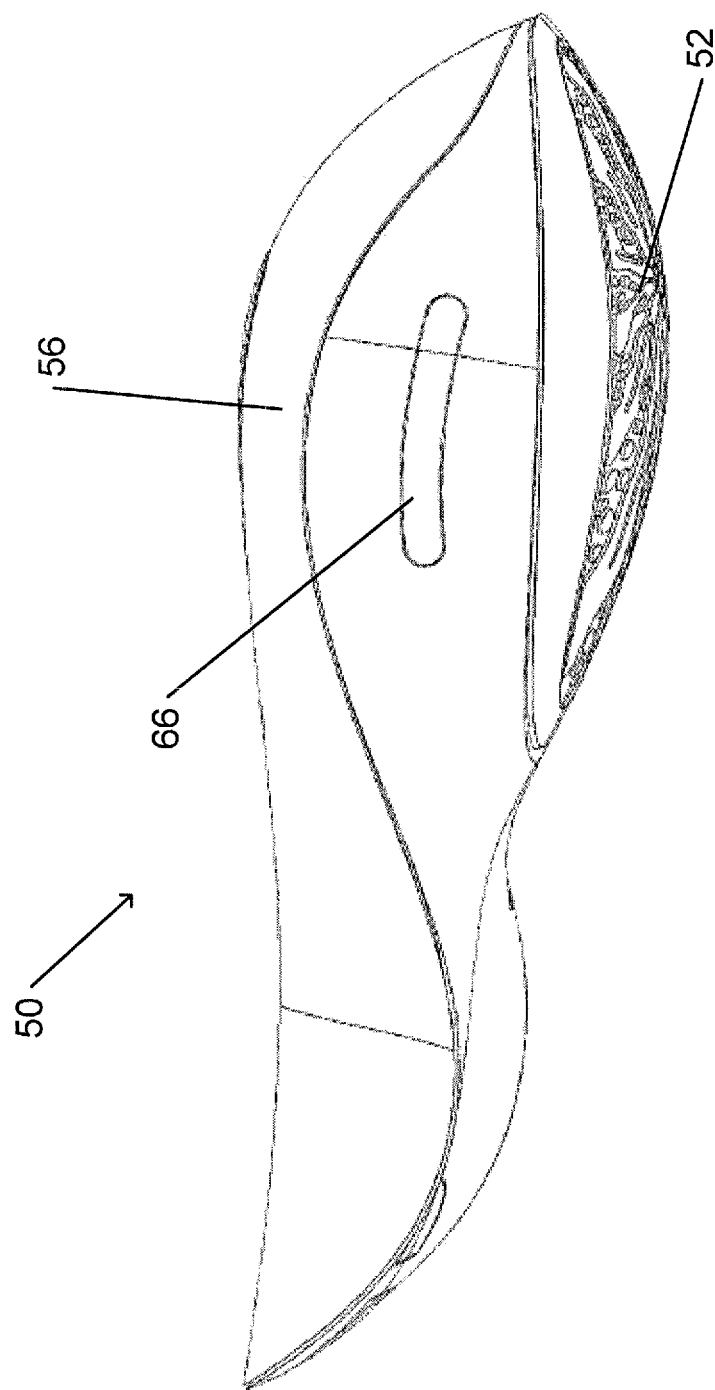
FIG. 2C shows another view of the transdermal delivery device shown in FIG. 2A.

FIG. 2A shows a transdermal delivery device in accordance with an embodiment of the present invention. FIG. 2B shows another view of the transdermal delivery device shown in FIG. 2A in which the iontophoresis electrode is visible. FIG. 2C shows another view of the transdermal delivery device shown in FIG. 2A.

Transdermal delivery device 50 may be configured primarily for self-application. For example, a user may hold transdermal delivery device 50 in one hand for delivery of an active ingredient of a substance to a different region of the user's skin. Transdermal delivery device 50 may also be operated so as to delivery the active ingredient to the skin of a patient who is not the user.

Transdermal delivery device 50 may include one or more controls 55. Controls 55 may be operated to control operation of transdermal delivery device 50. For example, operation of a control 55 may control a substance dispensing mechanism or operation of an electrical system for charging an iontophoresis electrode. A control 55 may serve as an indicator. For example, a light source (e.g. light emitting diode) that is embedded in a control 55 may be operated to indicate a current state of that control 55.

Transdermal delivery device 50 includes delivery plate 52. Delivery plate 52 is configured to be placed against the skin. When placed against the skin, delivery plate 52 may apply onto the skin and apply an electrical field to a substance that is dispensed from an installed canister. Transdermal delivery device 50 may be operated by operating user controls 54. An installed canister of a substance to be dispensed may be accessed, e.g. for removal or replacement, by opening one or more sections of cover 56. An installed canister may be viewed (e.g. to ascertain a quantity of the substance that remains in the canister) via window 66.

Transdermal delivery device 50 may be connected to another device via connector 58. For example, connector 58 may represent a power connection to which an electrical power cord may be attached. The electrical power cord may attach transdermal delivery device 50 to an external power source, such as an electrical power grid, or an external voltage or current source. The external power source may provide electrical power for operation of transdermal delivery device 50, or may provide electrical power for charging an internal power source (e.g. storage or rechargeable battery, or a capacitor) of transdermal delivery device 50.

Delivery plate 52 includes a system of substance distribution channels 60. Substance distribution channels 60 are configured to distribute a substance that is dispensed by an installed canister at opening 64 to a wider area of delivery plate 52. Substance distribution channels 60 are approximately radially interspersed among iontophoresis electrodes 62. Iontophoresis electrodes 62 may be charged so as generate an electric field for iontophoresis. Iontophoresis electrodes 62 may be electrically isolated from substance distribution channels 60.

All or part of a surface of an iontophoresis electrode 62 may be roughened. The roughening may enable the iontophoresis electrode 62 to facilitate exfoliation of the skin when the iontophoresis electrode 62 is moved along the skin.

A user operating transdermal delivery device 50 may hold return electrode plate 54. When holding return electrode plate 54 and when transdermal delivery device 50 is self applied, an electrical circuit may be completed via iontophoresis electrodes 62, the user's skin, and return electrode plate 54. When transdermal delivery device 50 is being applied by a user to another patient, return electrode plate 54 may be placed in contact with part of the patient's skin (e.g. a hand of the patient), or an electrode that is in electrical contact with return electrode plate 54 may be placed in contact with the patient's skin.

Figure 3:
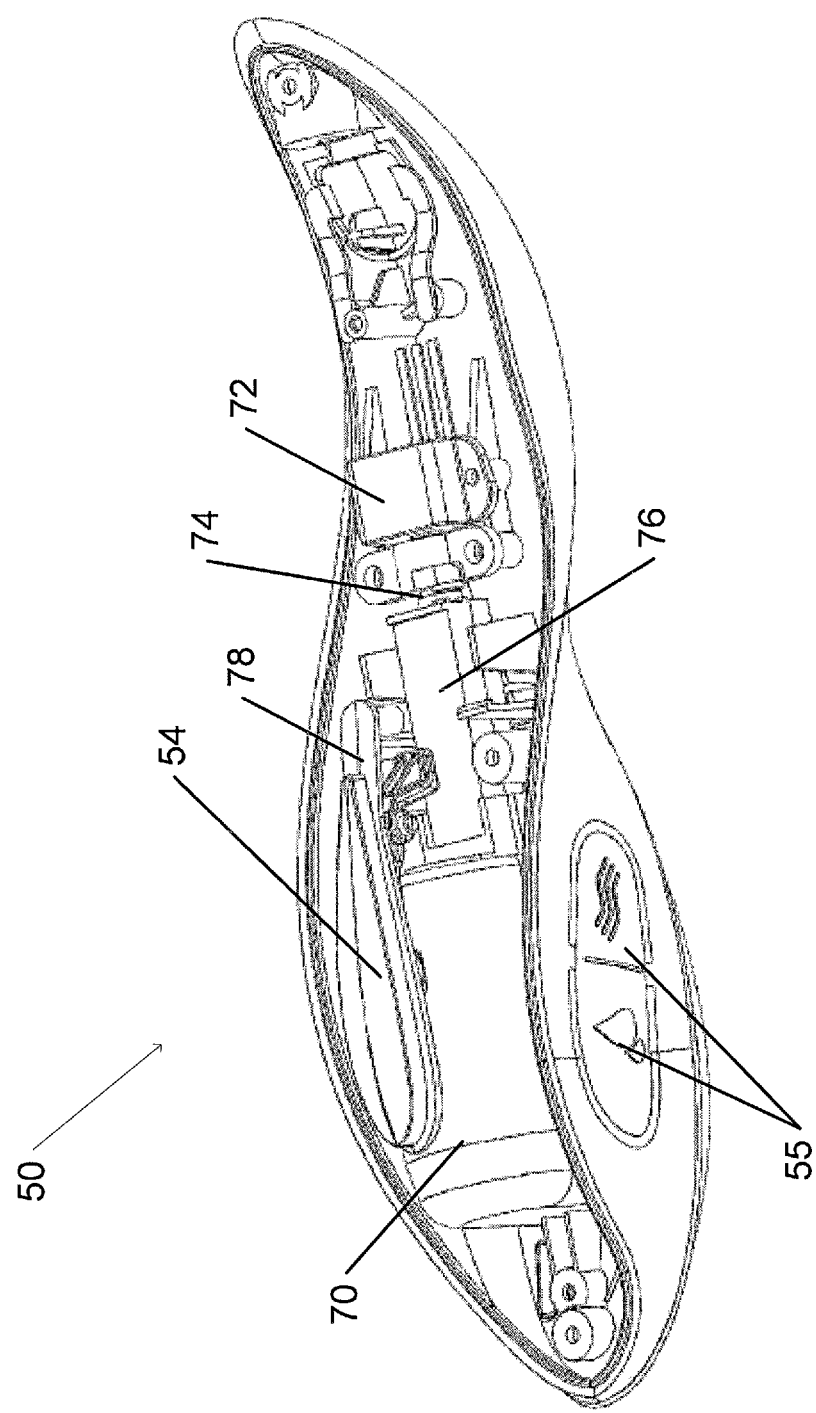
FIG. 3 shows internal components of the transdermal delivery device shown in FIG. 2A.

FIG. 3 shows internal components of the transdermal delivery device shown in FIG. 2A. In FIG. 3, cover 56 has been removed.

Canister cover 70 at least partially encloses a canister for holding a substance to be applied to the skin. Canister cover 70 may be held in place by locking bar 78. Locking bar may be opened (e.g. rotated away from canister cover 70) when canister cover 70 is removed, and closed (e.g. rotated such that a distal end of locking bar 78 presses against or engages canister cover 70) when canister cover 70 is to be held in place.

Canister cover 70 may be part of a replaceable canister, and is thus itself replaced when the canister is replaced. Alternatively, canister cover 70 may be part of transdermal delivery device 50. In this case, locking bar 78 may be opened, and canister cover 70 may be removed or opened, prior to removing the canister from transdermal delivery device 50. After a new or refilled canister is installed in transdermal delivery device 50, canister cover 70 may be returned or closed and locking bar 78 may be locked.

A substance dispensing mechanism of transdermal delivery device 50 includes a motor 72, and a transmission that includes worm 74 and a corresponding nut 76.

Figure 4:
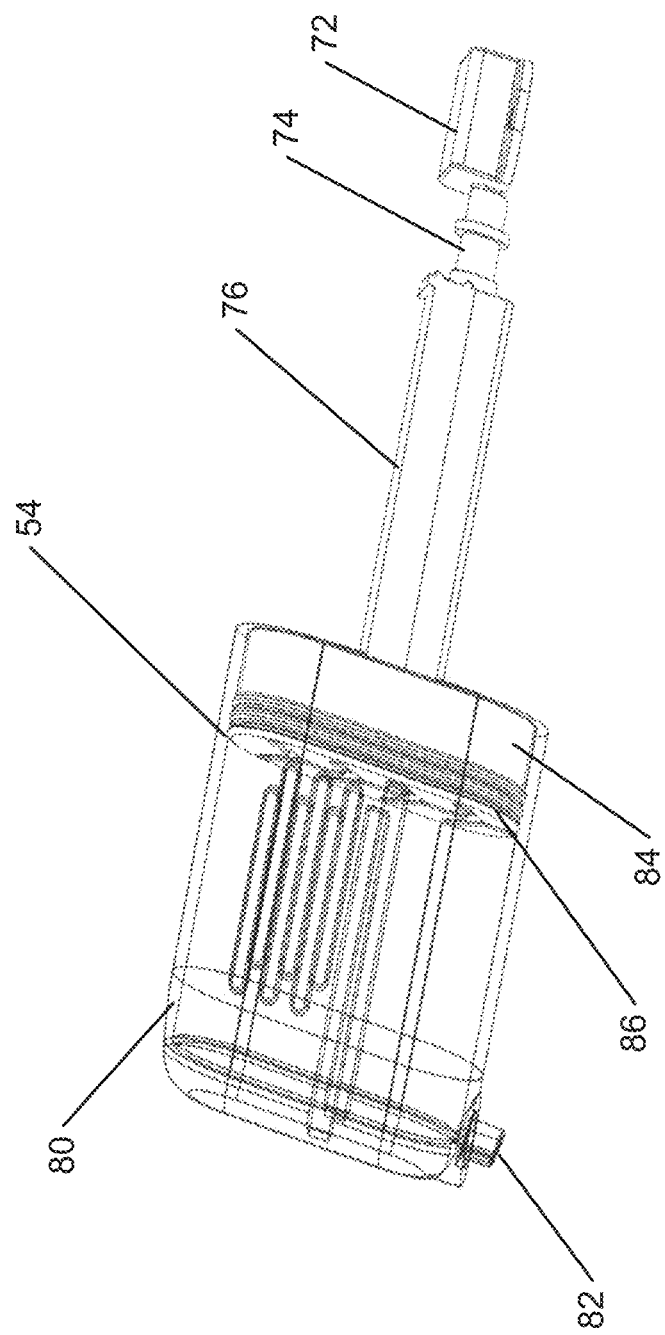
FIG. 4 shows components of a substance dispensing mechanism of the transdermal delivery device shown in FIG. 3.

FIG. 4 shows components of a substance dispensing mechanism of the transdermal delivery device shown in FIG. 3.

Motor 72 may be operated to rotate worm 74 about its axis. Rotation of worm 74 may move nut 76 longitudinally along worm 74.

Operation of motor 72 to rotate in a forward direction of rotation may cause nut 76 to move toward canister 80. When moving toward canister 80, piston 84 is pushed into canister 80. For example, piston 84 may be attached to nut 76, or a surface of nut 76 may push against piston 84.

Pushing piston 84 into canister 80 applies fluid pressure to a substance that is contained in canister 80. Piston seal 86 is configured to prevent the substance from seeping out of canister 80 between piston 84 and a wall of canister 80. Application of pressure to the substance in canister 80 so as to increase the fluid pressure of the substance may force a quantity of the substance out of canister spout 82. For example, canister spout 82 may be configured to self-seal when in the absence of increased pressure. Continuous pushing of piston 84 may cause the substance to be dispensed via canister spout 82 at a corresponding rate. If the substance in canister 80 in incompressible, pushing piston 84 to reduce the internal volume of canister 80 causes a similar volume of the substance to be dispensed via canister spout 82.

Prior to replacing canister 80, motor 72 may be operated in a reverse direction. Operation of motor 72 in the reverse direction may retract nut 76 (and piston 84, if attached to nut 76) from canister 80. Retraction of nut 76 from canister 80 may enable removal of canister 80 from the transdermal delivery device without interference from nut 76.

A transdermal delivery device in accordance with embodiments of the present invention may be utilized for execution of a method for transdermal delivery of an active ingredient. A cartridge or canister of the substance that includes the active ingredient may be installed, or may have been previously installed, in the transdermal delivery device.

A surface of the transdermal delivery device that includes an opening for dispensing the substance and an iontophoresis electrode are placed against the skin.

A substance dispensing system may be operated so as to dispense the substance onto the skin. For example, a control may be operated by a user so as to cause the substance to be dispensed onto the skin. Operation of the control may cause a predetermined quantity of the substance to be automatically dispensed, or a user may operate the control to initiate and terminate dispensing of the substance. A predetermined quantity may be determined on the basis of identification of the substance that is contained in the canister.

An electrical system may be operated to charge an appropriate iontophoresis electrode. For example, a control may be operated so as to charge the electrode. Operation of the control may charge the iontophoresis electrode to a predetermined charge for a predetermined period of time, or a user may operate the control so to control charging and discharging of the electrode. A predetermined charge or a predetermined time may be determined on the basis of identification of the substance that is contained in the canister. Charging the electrode concurrently with, or subsequent to, dispensing of the substance may cause transdermal delivery of an active ingredient of the substance via iontophoresis.

During operation of the electrical system, a return electrode may be placed in contact with a region of the skin that is not in contact with the electrophoresis electrode.

After operation of the transdermal delivery device to dispense the substance onto the skin and to apply iontophoresis to cause transdermal delivery of an active ingredient of the substance, the surface of the transdermal delivery device that includes the opening for dispensing the substance and the iontophoresis electrode may be moved to another region of the skin. Dispensing of the substance and application of iontophoresis may be repeated at the other location.

The invention claimed is:

1. A transdermal delivery device comprising:
a canister that includes an elongated spout through which a substance is dispensable from the canister;
a housing in which the canister is configured to be installed and replaced, the housing including a dispensing mechanism that is operable to dispense the substance from the canister through the spout when the canister is installed in the housing; and
a plate of the housing having an external surface that is placeable against skin, the external surface including a plurality of channels that radiate from an opening in the plate, the spout, when the canister is installed in the housing, being configured to extend outward through the opening to the external surface of the plate so as to dispense the substance directly from the canister onto the skin without an intervening conduit, the channels configured to distribute the substance over the plate, the plate including at least one iontophoresis electrode that is chargeable to generate an electric field to enable transdermal delivery of an active ingredient of the substance when the substance is dispensed onto the skin by the spout when the external surface of the plate is placed on the skin.

2. The device of claim 1, wherein the dispensing mechanism comprises an electric motor.

3. The device of claim 1, wherein the dispensing mechanism comprises a worm and a nut.

4. The device of claim 1, wherein the dispensing mechanism is configured to push a piston into the canister.

5. The device of claim 1, wherein the plurality of channels is electrically isolated from said at least one iontophoresis electrode.

6. The device of claim 1, wherein the dispensing mechanism is controllable to dispense a predetermined quantity of the substance.

7. The device of claim 1, wherein a charge that is applied to said at least one iontophoresis electrode is adjustable.

8. The device of claim 1, comprising a return electrode that is configured such that when said at least one iontophoresis electrode and the return electrode are placed in contact with separate regions of the skin, the skin completes an electrical circuit between the iontophoresis electrode and the return electrode.

9. The device of claim 8, wherein the return electrode is placed on an outer surface of the device such that when the device is held in a hand, the hand contacts the return electrode.

10. The device of claim 1, wherein a surface of said at least one iontophoresis electrode is roughened.

11. A method for transdermal delivery of an active ingredient of a substance, the method comprising:
installing a replaceable canister in a housing of a transdermal delivery device such that a spout of the canister extends outward through an opening in a plate of the housing to an external surface of the plate;

operating a dispensing mechanism of the housing so as to dispense the substance from the canister directly, without an intervening conduit, onto a region of skin via the spout and the opening to the external surface and via a plurality of channels on the external surface that radiate outward from the opening, the substance comprising an active ingredient with ionized molecules; and operating an iontophoresis electrode on the external surface of the plate when the iontophoresis electrode is in contact with the region of the skin to electrically charge the iontophoresis electrode with a charge whose sign is identical to a sign of a charge of the ionized molecules.

12. The method of claim 11, wherein operating the dispensing mechanism comprises operating the dispensing mechanism to dispense a predetermined quantity of the substance.

13. The method of claim 12, wherein the predetermined quantity is determined in accordance with a sensed characteristic of the skin.

14. The method of claim 13, wherein the characteristic is selected from a group of characteristics consisting of temperature, moistness, impedance, and conductance.

15. The method of claim 11, further comprising placing a return electrode of the device in contact with a region of the skin that is separated from the region of the skin where the iontophoresis electrode is placed.

16. The method of claim 15, comprising measuring an electrical current between the iontophoresis electrode and the return electrode.

\* \* \* \* \*